US 9,846,150 B2

(12) United States Patent
Jung et al.

(10) Patent No.: US 9,846,150 B2
(45) Date of Patent: Dec. 19, 2017

(54) HIGH EFFICIENCY PARTICLE SEPARATING APPARATUS AND METHOD

(75) Inventors: Hyo Il Jung, Seoul (KR); Ki Ho Kwon, Seoul (KR); Hui Sung Moon, Seoul (KR); Joo Hyuk Sohn, Seoul (KR); Seung Il Kim, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 684 days.

(21) Appl. No.: 14/123,473

(22) PCT Filed: Aug. 8, 2011

(86) PCT No.: PCT/KR2011/005753
§ 371 (c)(1),
(2), (4) Date: Dec. 4, 2013

(87) PCT Pub. No.: WO2012/165711
PCT Pub. Date: Dec. 6, 2012

(65) Prior Publication Data
US 2014/0102948 A1     Apr. 17, 2014

(30) Foreign Application Priority Data

Jun. 2, 2011   (KR) .................. 10-2011-0053363
Jun. 15, 2011  (KR) .................. 10-2011-0057766

(51) Int. Cl.
*G01N 33/483*   (2006.01)
*H04N 13/04*    (2006.01)
*G09G 3/00*     (2006.01)

(52) U.S. Cl.
CPC ..... *G01N 33/4836* (2013.01); *H04N 13/0418* (2013.01); *G09G 3/003* (2013.01); *H04N 13/0406* (2013.01)

(58) Field of Classification Search
CPC ............................. B03C 5/00–5/028
See application file for complete search history.

(56) References Cited

U.S. PATENT DOCUMENTS 5,993,630 A * 11/1999 Becker .................. B03C 5/028
                                               204/547
6,596,143 B1 * 7/2003 Wang .................... B01D 57/02
                                               204/450

(Continued)

FOREIGN PATENT DOCUMENTS

JP       2010-253410 A      11/2010
KR    10-2005-0047516 A      5/2005

(Continued)

OTHER PUBLICATIONS

Park, J. "Multiorifice Flow Fractionation: Continuous Size-Based Separation of Microspheres Using a Series of Contraction/Expansion Microchannels", Anal. Chem 2009 (81) pp. 8280-8288.*

(Continued)

*Primary Examiner* — Sean E Conley
*Assistant Examiner* — Matthew Krcha
(74) *Attorney, Agent, or Firm* — LRK Patent Law Firm

(57) ABSTRACT

A particle separating apparatus and method are provided, which pass a fluid sample such as blood through a filter to remove foreign matter, and separate target particles by using a MOFF channel, and re-separate the separated target particles through dielectrophoresis. The particle separating apparatus includes a MOFF (Multi Orifice Flow Fractionation) channel including a multi orifice segment through which a fluid sample passes to discharge a primarily separated material that are target particles separated from the fluid sample, through a central passage; a dielectrophoresis channel including a pair of electrodes to which AC power is applied and forming an electric field in a flow channel connected to the central passage of the MOFF channel to (Continued)

re-separate the target particles from the primarily separated material discharged from the central passage of the MOFF channel through dielectrophoresis.

10 Claims, 11 Drawing Sheets

(56) References Cited

U.S. PATENT DOCUMENTS

| | | | | |
|---|---|---|---|---|
| 7,811,439 | B1* | 10/2010 | Simmons | B01D 61/145 |
| | | | | 204/643 |
| 2005/0211556 | A1* | 9/2005 | Childers | B03C 5/005 |
| | | | | 204/518 |
| 2008/0283402 | A1* | 11/2008 | Peach | B01L 3/502761 |
| | | | | 204/547 |
| 2008/0318324 | A1 | 12/2008 | Chiu et al. | |

FOREIGN PATENT DOCUMENTS

| | | |
|---|---|---|
| KR | 10-2009-0092138 A | 8/2009 |
| KR | 10-0942364 B1 | 2/2010 |
| KR | 10-2010-0111097 A | 10/2010 |
| KR | 10-1133288 B1 | 4/2012 |

OTHER PUBLICATIONS

Park, J. "Continuous focusing of microparticles using inertial lift force and vorticity via multi-orifice microfluidic channels" Lab on a Chip 2009 (9) pp. 939-948.*

International Search Report for International Application No. PCT/KR2011/005753.

Moon, Hui Sung et al., "Continuous Separation of Breast Cancer Cells From Blood Samples Using Multi-Orifice Flow Fractionation (MS-MOFF) and Dielectrophoresis (DEP)", The Royal Society of Chemistry 2011, vol. 11, pp. 1118-1125, Published on the web Feb. 7, 2011.

Moon, Hui Sung et al., "Continuous Separation of Breast Cancer Cells From Blood Samples Using Multi-Orifice Flow Fractionation (MOFF) and Dielectrophoresis (DEP)", The Royal Society of Chemistry 2011, vol. 11, pp. 1118-1125, Published on the web Feb. 7, 2011.

Sim, Tae Seok et al., "Multistage-Multiorifice Flow Fractionation (MS-MOFF): Continuous Size-based Separation of Microspheres Using Multiple Series of Contraction/Expansion Microchannels", The Royal Society of Chemistry 2011, vol. 11, pp. 93-99, Published on the web Oct. 19, 2010.

* cited by examiner

HIGH EFFICIENCY PARTICLE SEPARATING APPARATUS AND METHOD

TECHNICAL FIELD

The present invention relates to a particle separation apparatus and method for separating target particles according to a fluid hydraulic method using a Multi-Orifice Flow Fractionation (MOFF) channel having a multi-orifice segment and separating the separated target particles again through dielectrophoresis, and more particularly, to high-efficiency particle separation apparatus and method for separating specific cells, for example, target particles, such as cancer cells, using an MOFF channel after alien substances are removed from a fluid sample, such as blood, through a filter and separating the separated specific cells again through dielectrophoresis.

BACKGROUND ART

Recently, researches on an MOFF channel having a multi-orifice segment have been reported.

However, such researches are only at the initial stage at home and abroad. In particular, the application of an MOFF channel to the medical world is in a very immaterial state.

Breast cancer is the first cancer rate in women even in Korea as well as in U.S.A. Lifetime incidence means a possibility that a specific disease will occur through life. In U.S.A., the lifetime incidence of breast cancer is 1/6, and one of 6 persons has breast cancer through lift.

In Korea, the frequency of an attack of breast cancer was about 20 persons per 100,000 persons 10 years ago, but breast cancer patients are suddenly increasing, that is, 50 persons or more per 100,000 persons in 2008. Furthermore, although the cause of breast cancer is not clear, in U.S.A., an attack of breast cancer increases with age and the most breast cancer occur in persons in the sixtieths~seventies, whereas in Korea, the most breast cancer occur in persons the 40's. A sudden increase of an attack rate and the most attack in the forties are a great social problem personally, domestically, and in terms of national economy.

In particular, breast cancer, unlike thyroid cancer frequently occurred in women, is not treated by only a surgical operation, but is cancer that requires a very complicated treatment process of 6 months to 1 year or more, such as anticancer drug treatment, hormone treatment, radiation treatment, and target treatment even after the operation. However, despite such various and long-term treatment, 30~40% of all breast cancer patients needs to experience medication again due to recurrence and metastasis. Nevertheless, most of patients whose cancer recurs lead up to death.

In the case of a cancer patient, the greatest influence on mortality depends on the presence or not of metastatic cancer cells. That is, technology in which one Circulating Tumor Cell (CTC) needs to be found in $10^9$ red cells within blood very precisely without a loss of a cell is much-needed technology in order to improve a survival rate before and after cancer treatment of patients.

In blood of about 7.5 ml, CTCs less than 5 need to be found in the case of breast cancer, CTCs less than 3 need to be found in the case of colorectal cancer, and CTCs less than 5 need to be found in the case of prostate cancer. Microcell separation technology that satisfy three basic conditions 1) throughput (the number of cells that may be separated per time), 2) cell recovery (a ratio of the number of injected target cells and the number of separated and recovered target cells), and 3) separation efficiency (purity, degree of purity of separated and recovered target cells) is necessary.

CTC metering methods disclosed so far may be classified into a genetic metering method using Polymerase Chain Reaction (PCR), a metering method using centrifugal separation and magnetophoresis, a fluorescent dyeing method, and a method using a filter. Most of the methods are disadvantageous in that reliability of diagnosis is low because target cells are lost due to a pre-processing process of removing a large number of blood cells included in blood in order to detect a CTC.

Representatively, CellSearch that was solely approved by FDA as a CTC diagnostic tool includes a pre-processing process for samples and an analysis process for refined samples. The pre-processing process is disadvantageous in that a CTC may be missed in a pre-processing step because it includes several steps along with a process of processing Anti-EpCAM using magnetic particles, mixing the Anti-EpCAM with the blood of a patient, and separating a CTC using magnetism. A loss of samples in detecting a CTC known to be present as one concentration in $10^9$ cells is an important problem that is directly connected to the accuracy of diagnosis.

Accordingly, there is a need for a microfluid system in which steps from a pre-processing process to the final diagnosis process are continuously integrated as a method using the size, density, and modification, that is, physical characteristics inherent in a CTC. Furthermore, a CTC separated using the microfluid system needs to be analyzed using optical equipment in real time, and a clinician must perform molecular analysis into the verified CTC.

A current anticancer adjuvant therapy is performed on almost most of patients without checking the presence or not of such a CTC. Anticancer drugs are equally administrated to patients based on the results of clinical tests because there is no method of checking whether or not such anticancer drug treatment help the patients individually. In fact, patients whose cancer recurs although anticancer drugs are not administrated to the patients exceed half of all breast cancer patients, but most of patients including such patients experience anticancer drug treatment because it is not known when cancer will recur in what patients.

A research hypothesis that unnecessary anticancer drug treatment can be reduced by selecting patients whose cancer may recur through detection and analysis researches into a CTC. Furthermore, by taking that fact that cancer recurs in 30~40% of all patients despite a surgical operation and an anticancer adjuvant therapy into consideration, it is determined that anticancer treatment effects will be more smooth only when anticancer drugs effective in a CTC, that is, the eventual cause of recurrence, are used. Accordingly, researches into the detection and analysis of a CTC are considered to be an important foundation in developing more effective anticancer drugs in the future.

In recent various molecular biological techniques, various types of cancer cells can be tested using a blood test. In particular, a method of finding and diagnosing a Circulating Tumor Cell (CTC) within blood, which is known as a cell that enters blood and circulates the body, from among cancer cells, is a very effective technique in early diagnosing a cancer patient and determining prognosis after treatment, but a successful case thereof is rare.

With the recent development of a molecular biological diagnostic method having high sensitivity, a clinical base that may be used in the molecular staging of cancer patients, the prediction of prognosis, and the early detection of recurrence. As various types of molecular biological schemes based on PCR are automated, the sensitivity of a test is improved, an analysis process is simplified, and an analysis time is reduced.

Accordingly, it is necessary to develop a system capable of separating and metering a CTC using blood samples obtained from a cancer patient. The development of such a system will help more understanding of a molecular structure of a cell that is necessary to check cancer through CTC researches and clarify the characteristics of a cancer cell and a cancer cell metastatic process.

DISCLOSURE

Technical Problem

An object of the present invention is to provide a particle separation apparatus and method, which separate target particles according to a fluid hydraulic method using a Multi-Orifice Flow Fractionation (MOFF) channel having a multi-orifice segment and separate the separated target particles again through dielectrophoresis (DEP).

Another object of the present invention is to provide a particle (cell) separation apparatus and method, which are capable of efficiently separating a greater amount within a short time using an MOFF channel and dielectrophoresis channels in order to separate cancer cells, that is, target particles (target cells), such as Circulating Tumor Cells (CTCs) within blood (e.g., CTCs of breast cancer and colorectal cancer, HT-29, or a cancer cell line, such as MCF-7), from a fluid sample, such as blood.

Yet another object of the present invention is to provide a high-efficiency particle separation apparatus and method, wherein target particles are separated using an MOFF channel and a dielectrophoresis channel and the MOFF channel is configured to pass through a multi-orifice segment after alien substances are removed from a fluid sample through a filter.

Technical Solution

A particle separation apparatus in accordance with an aspect of the present invention includes a Multi-Orifice Flow Fractionation (MOFF) channel including a multi-orifice segment through which a fluid sample passes and discharging primarily separated materials from which target particles within the fluid sample have been separated through a central passage; and a dielectrophoresis channel including a pair of electrodes to which AC power is applied, forming an electric field in a flow channel connected to the central passage of the MOFF channel, and separating the target particles from the primarily separated materials discharged from the central passage of the MOFF channel again using dielectrophoresis.

Furthermore, in the present invention, a particle separation apparatus for separating target particles using an MOFF channel having a multi-orifice segment and separating the target particles again through a dielectrophoresis channel includes a filter removing alien substances from a fluid sample inputted to an inlet; and a first separation unit discharging a fluid sample, including a plurality of the target particles, to a central passage after the fluid sample passing through the filter passes through the multi-orifice segment, and discharging a fluid sample, including a plurality of particles other than the target particles, to passages on both sides thereof.

Furthermore, in the present invention, in a particle separation apparatus for separating target particles using an MOFF channel having a multi-orifice segment and separating the target particles again through a dielectrophoresis channel, the MOFF channel includes a focusing unit equipped with one or more first electrode pairs to which AC power is applied and configured to have target particles of a fluid sample, separated from the MOFF channel, concentrated at a center of the flow channel; and a second separation unit equipped with one or more second electrode pairs to which the AC power is applied, wherein the second pair of electrodes is symmetrical with the first pair of electrodes, and the target particles are separated by an electric field.

The first electrode has a '<' shape, and the second electrode has a '>' shape.

The central passage has a greater diameter within the passage from the entrance thereof to the exit thereof.

The AC power is selectively applied in a range of a frequency 100~900 kHz within a range of 10~100 volts.

The target particle may be a cell, the cell may be a Circulating Tumor Cell (CTC), and the CTC may be a CTC of breast cancer or colorectal cancer, HT-29, or a cancer cell line of MCF-7.

The target particles may include any one of red cells, emulsion red cells, and multiple osteomyelitis or multiple myeloma.

The target particles may be stem cells, and the particle separation apparatus may be configured to separate stem cells from a fluid in which stem cells and normal cells are mixed.

The target particles may be bacteria, and the particle separation apparatus may be configured to separate bacteria from a fluid in which dust and bacteria are mixed.

Furthermore, a particle separation apparatus of the present invention includes a Multi-Orifice Flow Fractionation (MOFF) channel having a first separation unit, including a central passage and passages on both sides thereof, formed at an end of a multi-orifice segment through which fluid sample passes; and dielectrophoresis channel combined with the central passage, wherein the dielectrophoresis channel includes a focusing unit including bent type first metal electrodes, having a power source supplied between odd electrodes and even electrodes, spaced apart from one another and disposed at specific intervals; and a second separation unit including bent type second metal electrodes symmetrically disposed along with the first metal electrodes and having a power source supplied between odd electrodes and even electrodes.

Particles of a fluid introduced into the dielectrophoresis channel through the central passage moves and flows from the focusing unit to both sides thereof, and target particles are drained to the center of the second separation unit.

AC power is supplied between the odd electrodes and the even electrodes of the first metal electrodes, and AC power is supplied between the odd electrodes and the even electrodes of the second metal electrodes.

The AC power may be in a range of a frequency 100~900 kHz within a range of 10~100 volts.

The particle separation apparatus may be used to separate target particles MCF-7 from a blood sample.

Each segment of the multi-orifice segment may have a horizontal length, a vertical length, and a height of 300× 300×60 (μm) in a progress direction of a wide part and have a horizontal length, a vertical length, and a height of 150×60×60 (μm) in a progress direction of a narrow part.

The MOFF channel includes a filter for removing alien substances between the multi-orifice segment and the inlet.

The filter includes a passage having a specific width through which the fluid sample passes between lattices, and the lattices include one or more lattices bent at right angles.

The MOFF channel includes a plurality of MOFF channels connected in parallel, for processing respective fluid samples branched from one inlet, and the central passages of the plurality of MOFF channels may be connected to one passage and combined with the dielectrophoresis channel.

The fluid sample may be a blood sample on which pre-processing has been performed using red cell hemoclastic.

Furthermore, a particle separation method in accordance with another aspect of the present invention includes the steps of passing a fluid sample through a multi-orifice segment of a Multi-Orifice Flow Fractionation (MOFF) channel and discharging the fluid sample to a central passage of a first separation unit including the central passage and passages on both sides thereof at an end of the multi-orifice segment; and discharging target particles by passing a fluid, discharged to the central passage of the first separation unit, through a focusing unit of a dielectrophoresis channel combined with the central passage and a second separation unit, wherein a power source is supplied between odd electrodes and even electrodes of bent type first metal electrodes spaced apart from one another and disposed in the focusing unit at specific intervals, and the power source is applied between odd electrodes and even electrodes of bent type second metal electrodes spaced apart from one another and disposed in the second separation unit at specific intervals symmetrically with the first metal electrodes.

Advantageous Effects

In accordance with the high-efficiency cell separation apparatus and method according to the present invention, target cells, such as Circulating Tumor Cells (CTCs) within blood (e.g., CTCs of breast cancer or colorectal cancer and a cancer cell line, such as MCF-7), can be more efficiently separated from a fluid sample, such as blood, by separating the target cells according to a fluid hydraulic method using a Multi-Orifice Flow Fractionation (MOFF) channel having a multi-orifice segment and separating the separated target cells again through dielectrophoresis (DEP).

Furthermore, the high-efficiency cell separation apparatus and method of the present invention can efficiently separate red cells, emulsion red cells, multiple osteomyelitis or multiple myeloma, can separate stem cells and normal cells, and can separate dust and bacteria.

Furthermore, the processing capabilities can be maximized by connecting a plurality of the MOFF channels, thereby improving throughput, the degree of purity of target cells, that is, separation efficiency, can be improved by separating alien substances from a fluid sample after the alien substances are removed through a filter, and cell recovery can be improved because target cells are efficiently separated by optimally designing the multi-orifice segment.

MODE FOR INVENTION

Hereinafter preferred embodiments of the present invention are described in detail with reference to the accompanying drawings and contents described in the accompanying drawings, but the present invention is not restricted or limited by the embodiments.

Technology in which cancer cells, that is, target particles, such as Circulating Tumor Cells (CTCs) (e.g., CTCs of breast cancer and colorectal cancer, HT-29, or a cancer cell line, such as MCF-7) within blood, are separated from a blood sample is described below, but the present invention is not limited thereto. It is to bed noted that a particle separation apparatus and method in accordance with an embodiment of the present invention may be likewise applied to fields, such as the detection of other disease-causing germs, the development of new medicines, a medicine test, and cell replacement treatment method in order to, separate other target particles, such as disease-causing germs and cells.

Figure 1:
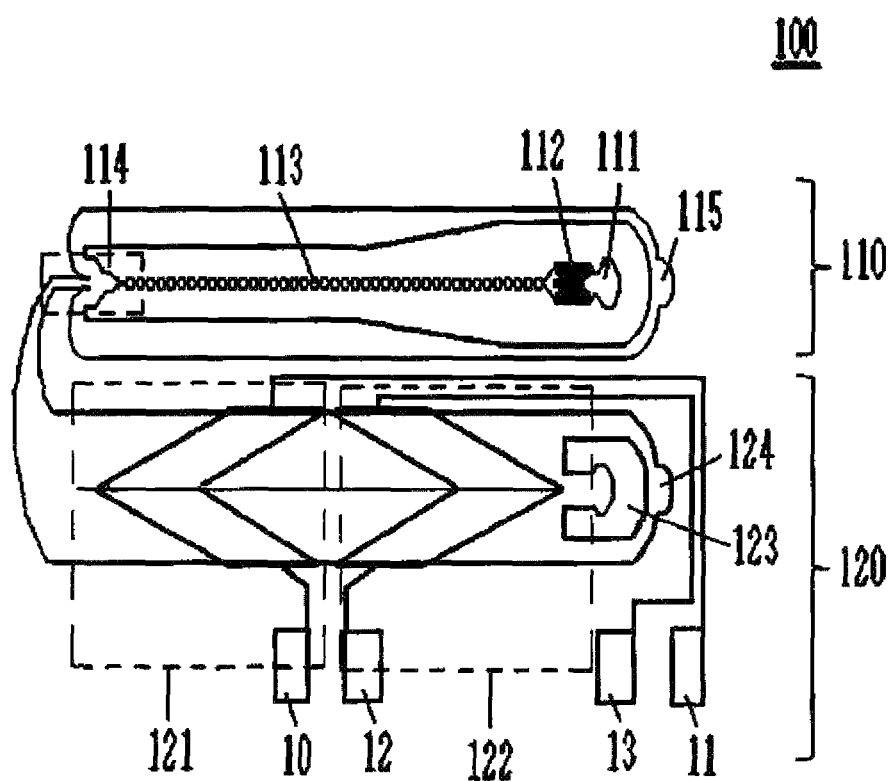
FIG. 1 is a diagram illustrating a cell separation apparatus in accordance with an embodiment of the present invention.
Figure 2:
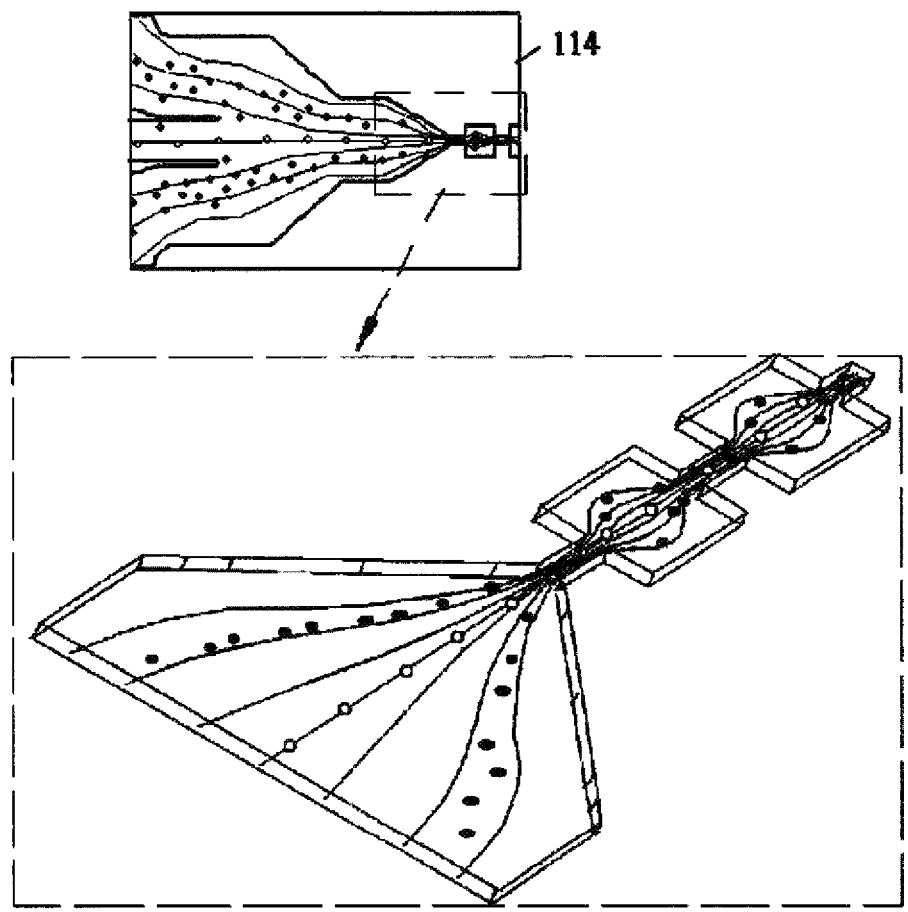
FIG. 2 is an enlarged view of the separation unit of an MOFF channel of FIG. 1.
Figure 3:
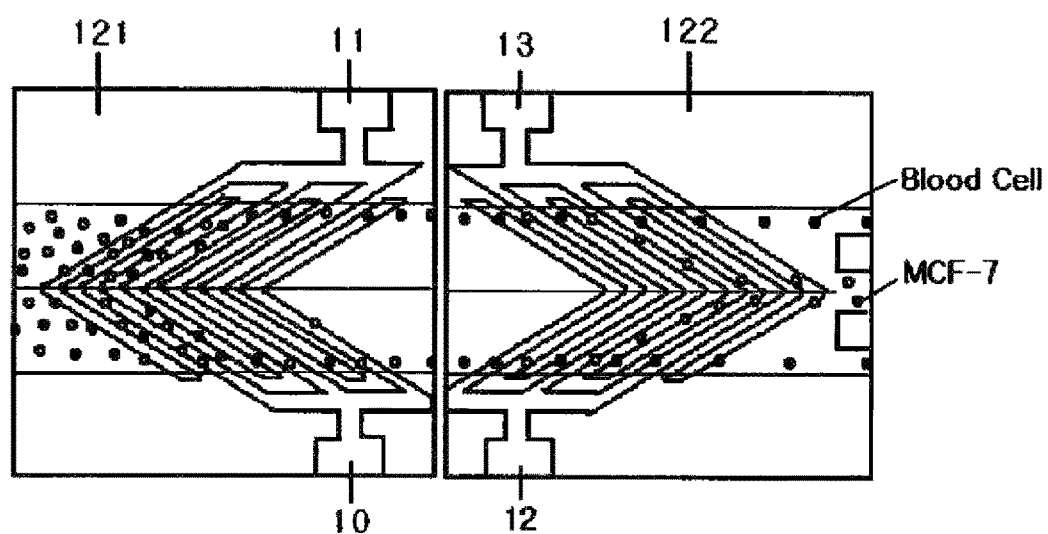
FIG. 3 is an enlarged view of a dielectrophoresis channel of FIG. 1.

FIG. 1 is a diagram illustrating a particle separation apparatus (cell separation apparatus) 100 in accordance with an embodiment of the present invention. Reference is made to FIG. 2, showing an enlarged view of the separation unit 114 of an MOFF channel 110 of FIG. 1, and FIG. 3 showing an enlarged view of a dielectrophoresis channel 120 of FIG. 1.

In FIG. 1, the particle separation apparatus 100 in accordance with an embodiment of the present invention includes the Multi-Orifice Flow Fractionation (MOFF) channel 110 and a dielectrophoresis (DEP) channel 120.

A fluid sample (blood sample) is inputted to the inlet 111 of the MOFF channel 110, a filter 112 removes alien substances from the fluid sample, the fluid sample passes through a multi-orifice segment 113, and the fluid sample is separated by the separation unit 114 formed at the end of multi-orifice segment 113. As shown in FIG. 2, blood including target particles, that is, a large number of target cells (e.g., MCF-7), is discharged through the central passage of the separation unit 114, and blood including a large number of blood cells (red cells/white corpuscles) is discharged through passages on both sides of the separation unit 114. The dielectrophoresis channel 120 is connected to the central passage of the separation unit 114, and the blood discharged through the passages on both sides of the separation unit 114 can be discharged through an outlet 115 and wasted.

The blood discharged to the central passage of the separation unit 114 is secondarily separated while passing through the focusing unit 121 and the separation unit 122 of the dielectrophoresis channel 120. Accordingly, target particles, that is, target cells, for example, MCF-7 can be drained from a central outlet 123 at the center of the end of the separation unit 122, and the blood discharged to the passages on both sides at the end of the separation unit 122 can be discharged through an outlet 124 and wasted.

As shown in FIG. 3, the focusing unit 121 includes bent type metal electrodes spaced apart from one another at specific intervals and curved in a '<' shape, wherein odd electrodes disposed in odd numbers and even electrodes disposed in even numbers are electrically isolated from each other, and AC power is applied to the odd electrodes and the even electrodes through electrode pads 10 and 11. The separation unit 122 also includes bent type metal electrodes spaced apart from one another at specific intervals and curved in a '>' shape. The bent type metal electrodes of the separation unit 122 are disposed symmetrically with the bent type metal electrodes of the focusing unit 121. In the bent type metal electrodes of the separation unit 122, odd electrodes disposed in odd numbers and even electrodes disposed in even numbers are electrically isolated from each other, and AC power is applied to the odd electrodes and the even electrodes through electrode pads 12 and 13. Here, the AC power applied between the odd electrodes and the even electrodes of the focusing unit 121 and the separation unit 122 may be selected in a range of a peak-peak 10~100 volts and a range of a frequency 100~900 kHz depending on the type of target particles cells).

In an actual blood sample, in the case of leukemia, a ratio of cancer cells is present at a very high concentration, but a very small number of other cancer cells (e.g., MCF-7) are present in a ratio of one cancer cell in $10^9$ cells. In order to such samples, a device having high throughput and excellent separation efficiency is essential. As a method of further improving the efficiency of a cell separator, in the present invention, fluid hydrodynamic using the MOFF channel 110 and dielectrophoresis using the dielectrophoresis channel 120 are grafted together as described above.

In separation based on fluid hydrodynamic, processing speed is rapid, but an actual cell size is not equal. Accordingly, a small number of blood cells (e.g., red cells/white corpuscles), together with cancer cells (e.g., MCF-7), flow into the central passage of the separation unit 114. Here, advantageous conditions are formed upon dielectrophoresis by reducing the moving speed of samples through a flow passage design.

The fluid sample flown into the dielectrophoresis channel 120 through the central passage of the separation unit 114 can be precisely separated depending on the dielectric characteristics (e.g., a difference in the dielectric constant) of cells. Most of blood cells have been primarily separated and removed by the MOFF channel 110, and thus cancer cells having a high degree of purity can be separated by secondarily precisely separating cancer cells through dielectrophoresis using the dielectrophoresis channel 120.

If the AC power is applied between the odd electrodes and the even electrodes of the focusing unit 121 and the separation unit 122 as described above so that an electric field having a specific frequency (e.g., 100~900 kHz) is formed, only cancer cells can be selectively filtered without filtering blood cells. As shown in FIG. 3, the cells of the fluid that have been flown through the central passage of the separation unit 114 can move and flow to both sides thereof in their progress direction due to the electric field at the bottom portion formed in the micro passage owing to the electrodes of the focusing unit 121. Since force (positive dielectrophotrtic force) that pulls only cancer cells (e.g., MCF-7) is generated due to the electric field at the bottom portion formed in the micro passage owing to the electrodes of the separation unit 122, the blood cells move and flow to both sides thereof without being subject to the force, and thus the blood cells can be discharged through the side outlet 124 and wasted. Furthermore, the target particles (cells), for example, MCF-7 pulled to the center of the separation unit 114 due to the electric field can be drained through the central outlet 123 at the end of the separation unit 122.

By separating the cells again according to a dielectrophoresis (DEP) method using the dielectrophoresis channel 120 after separating the cell according to a fluid hydraulic method using the MOFF channel 110 as described above, cancer cells, that is, target particles (cells), such as Circulating Tumor Cells (CTCs) (e.g., MCF-7) within blood, can be more efficiently separated from the fluid sample, such as blood. Through such twice separation processes, 162.4 times enrichment effects were successfully obtained by removing blood cells of 99% and only selectively separating only cancer cells within blood as in Table 1. In Table 1, the outlet I corresponds to the outlet 115 of the MOFF channel 110, and the outlets II and III correspond to the outlet 123 and the outlet 124 of the dielectrophoresis channel 120.

In accordance with such a method, cell recovery can be significantly improved as compared with a drain method using an antibody, and cancer cells can be obtained at faster speed than that in an existing microfluid system. As described above, a method of separating blood and cancer cells according to a label-free method using hydrodynamic and micro fluids corresponding to epochal technology that is not present.

TABLE 1

| Sample name | | RBC | WBC | MCF-7 |
| --- | --- | --- | --- | --- |
| Recovery | Outlet II | 0.76 | 5.77 | 75.81* |
|  | Outlet I + III | 99.24* | 94.23* | 24.19 |
| Purity | Outlet II | 80.62 | 3.14 | 16.24** |
|  | Outlet I + III | 98.24 | 1.45 | 0.31 |

*Final recovery of each cell. 75.81% of MCF-7 cells were isolated using our MOFF-DEP device, while 99.24% of RBCs and 94.23% of WBCs were removed.
**The final fraction of MCF-7 cells from the separated sample. Since the fraction of MCF-7 at the introduced sample was 0.1%, the enrichment factor was 162.4.

Figure 4:
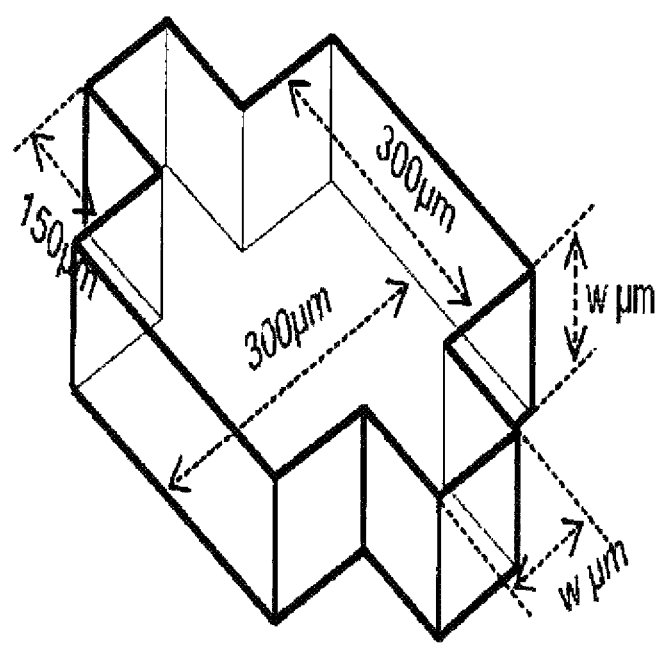
FIG. 4 a diagram illustrating of each segment of the multi-orifice segment of the MOFF channel of FIG. 1.

Meanwhile, each of the segments of the multi-orifice segment 113 of the MOFF channel 110 of FIG. 1 can be designed as in FIG. 4. Wide parts and narrow parts are repeated plural times and connected to each segment of the multi-orifice segment 113 of the MOFF channel 110. Experiments were performed based on a horizontal length, a vertical length, and a height of 300*300*w (μm) in the progress direction of the wide part and based on a horizontal length, a vertical length, and a height of 150*w*w (μm) in the progress direction of the narrow part by changing w.

Cells that occupy the greatest ratio in blood cells are red cells (RBC), and the red cell has a disk shape and has a thickness of 2~3 μm and a diameter of about 7~8 μm. White corpuscles (WBC) are various in type, and the size and distribution of white corpuscles are not uniform as compared with red cells. However, neutrophils and lymphocytes that occupy a major ratio in white corpuscles have a distribution of about 7~12 μm in each size. In contrast, a MCF-7 cell selected as a model of a cancer cell, that is, target particles (cell) to be separated has an average size of about 20 μm, and the MCF-7 cells have a greater distribution than blood cells.

The size of the MOFF channel 110 was required to be changed so that such cells can be most separated. Here, the shape of the MOFF channel 110 was determined based on particle Reynold's number that is closely related to the behavior of particles within the channel. A representative size of a blood cell set to 8 μm (a dotted line of FIG. 5) and an MCF-7 set to an average size of 20 μm (a solid line of FIG. 5) were used as criteria for a change of the channel design.

Figure 5:
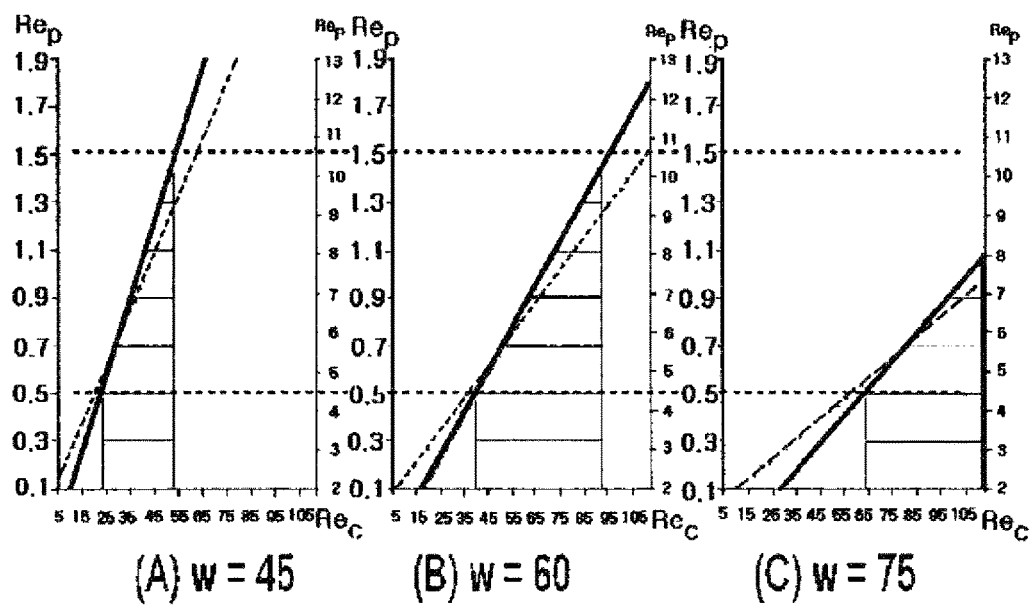
FIG. 5 is a graph illustrating critical Reynold's number for illustrating a fluid velocity region in which blood cells according to a length w of FIG. 4 and MCF-7 can be separated.

FIG. 5 is a graph illustrating critical Reynold's number (Rec) for illustrating a fluid velocity region in which blood cells and MCF-7 can be separated depending on a length w in relation to a blood sample having constant viscosity. Rep and Rec have the same relation as Equation 1, which indicate critical Reynold's number (Rec) for Reynold's number Rep 4.43~10.1 in relation to CF-7 cells and indicate critical Reynold's number (Rec) for Reynold's number Rep 0.55~1.38 in relation to blood cells. Here, $D_n$ is a hydraulic diameter determined by the design of a segment of the channel, d is a total channel length, Um is a maximum flow velocity, ρ is fluid density, and μ is fluid dynamic viscosity.

$$Re_p = Re_c \frac{d^2}{D_h^2} = \frac{\rho U_m d^2}{\mu D_h} \quad \text{Equation 1}$$

Since a stable separation condition can be guaranteed in specific flow velocity according to an increase of the separation region, the design of (B) (when w=60 μm) or (C) (when w=75 μm) can be said to be more stable as compared with (A) (when w=45 μm) in FIG. 5. However, such a separation section is further increased as the width of the channel is widened. It can be checked that the flow velocity condition in which simultaneous separation is possible varies according to a unique amount. If the amount of an operating fluid is increased, the design needs to be determined under a condition that minimizes the influence of cells because share stress that affects cells is also increased. Accordingly, in the present invention, an optimal design was determined to be w=60 μm in a contraction channel.

Figure 6:
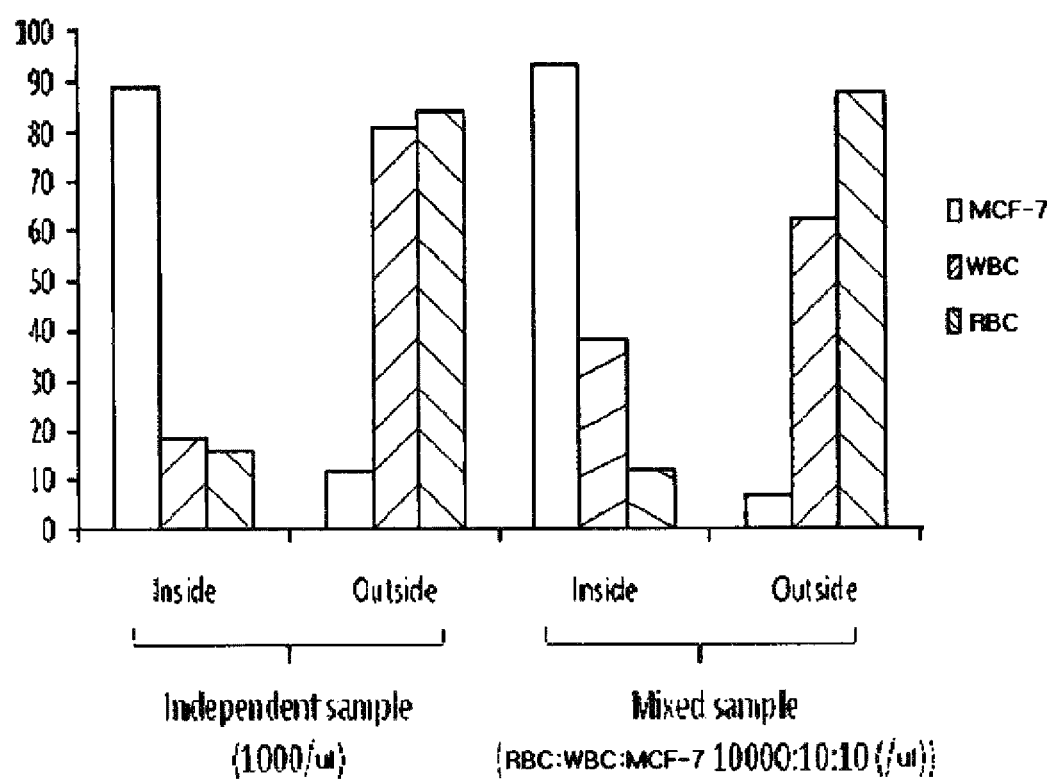
FIG. 6 is a graph showing cell recovery in w=60 μm in FIG. 4.

As a result of experiments for the vein blood of a healthy person, it could be seen that the behaviors of RBC and WBC were similarly changed according to a change of flow velocity if RBC and WBC have a similar size distribution. RBC and WBC flow through the MOFF channel 110 (segments) without directivity at low flow velocity, and when channel Reynold's number (Rec) reaches 70 as the low velocity becomes gradually fast, RBC and WBC are divided into both sides (outside) of the channel and flown. However, it was checked that MCF-7 having a larger size than RBC and WBC gathers at the central passage (inside) of the separation unit 114 in the same flow velocity and flows, so blood cells and MCF-7 are clearly separated. In such experiments, if w=60 μm in each segment of the multi-orifice segment 113 of the MOFF channel 110 as in FIG. 6, it could be seen that cell recovery of 88.8% of MCF-7 cells was obtained in a blood sample (left graph) and similar results were checked in the results of mixed samples (right graph). However, in the case of blood cells, separation efficiency of WBC was slightly reduced when the blood cells were mixed with samples and subject to experiments. This is because an interaction was generated between cells in the samples of a high concentration.

Figure 7:
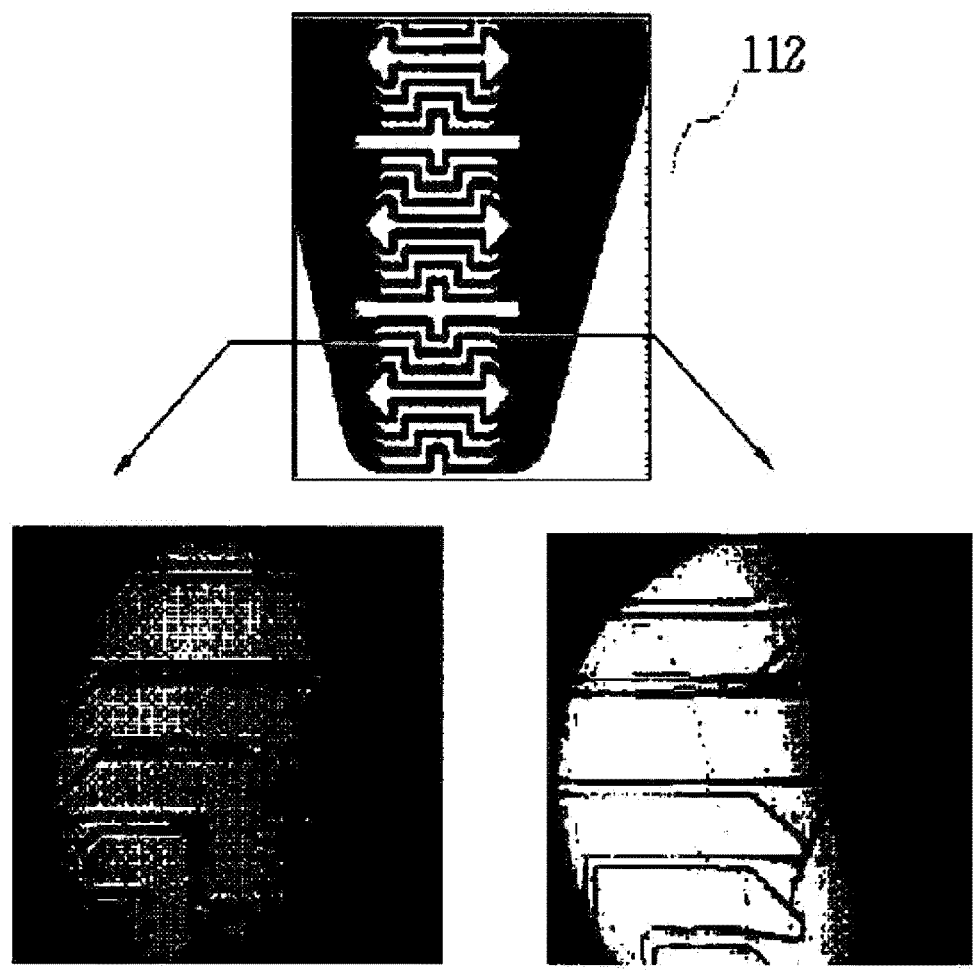
FIG. 7 is a diagram illustrating a filter that is formed in the inlet of the MOFF channel in accordance with an embodiment of the present invention.
Figure 8:
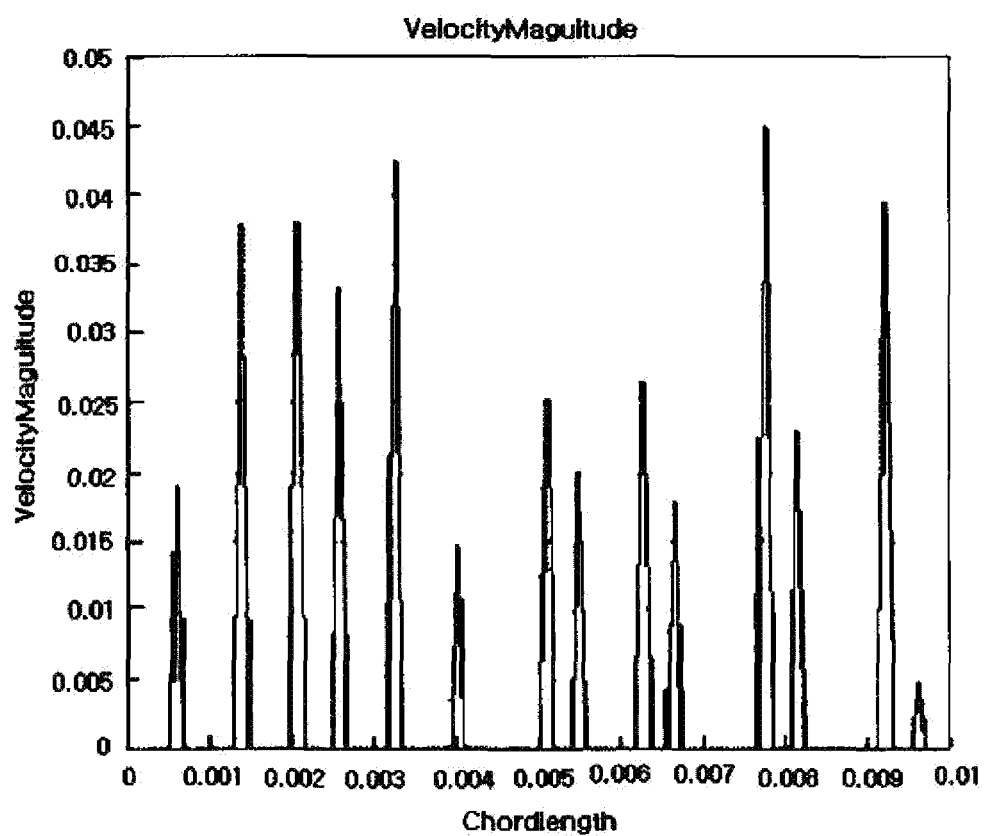
FIG. 8 is a graph showing flow velocity of a fluid when the filter of FIG. 7 is used.

FIG. 7 is a diagram illustrating the filter 112 formed between the inlet 111 and the multi-orifice segment 113 of the MOFF channel 110 in accordance with an embodiment of the present invention. The filter 112 for reducing the time taken to prepare samples additionally by automatically removing alien substances, such as floating duct included in a blood sample include lattices disposed at specific intervals in a row, a passage of a specific width through which blood (fluid) samples pass is formed between the lattices, and one or more lattices bent at right angles are included in the lattices. Accordingly, since alien substances, such as floating dust within blood, are filtered and easily removed while passing through the bent type channels, a problem in that alien substances are introduced into the multi-orifice segment 113 of the MUFF channel 110 and thus alien substances block the channel can be prevented. A maximum number of lattices bent at right angles, such as a cross and a 'ᄃ' shape, one or more times, from among the lattices, may be disposed in order to minimize influence subject to cells when the cells pass through the filter 112. Simulation results show that cells pass through the filter 112 at slow velocity as in FIG. 8.

Figure 9:
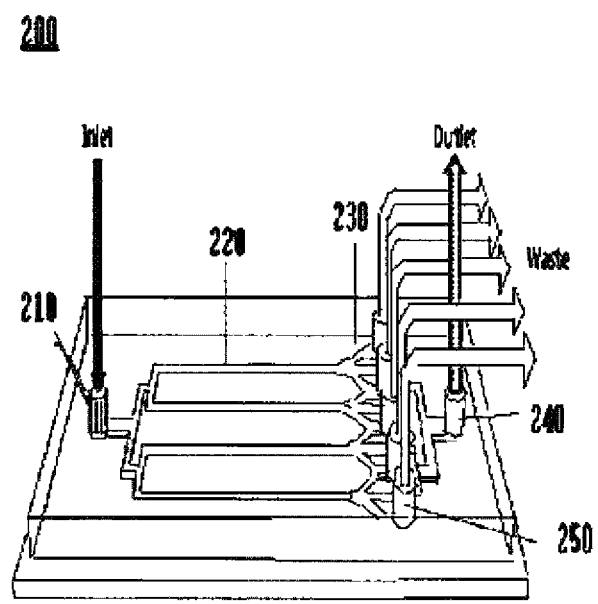
FIG. 9 is a diagram illustrating parallel MOFF channels in accordance with an embodiment of the present invention.

FIG. 9 is a diagram illustrating parallel MOFF channels 200 in accordance with an embodiment of the present invention. The MOFF channel 110 of FIG. 1 may be replaced with MOFF channels 200 in parallel connected as in FIG. 9. For example, a plurality of MOFF channels 200 in parallel connected for processing fluid (blood) samples branched from one inlet 210 can be used. Here, central passages included in the respective separation units 230 of the plurality of MOFF channels 200 can be connected to one passage 240 and connected to the dielectrophoresis channel 120 of FIG. 1. Blood discharged to the passages on both sides at the end of the separation units 230 of the plurality of MOFF channels 200 can be discharged through another outlet and wasted.

The MOFF channel 110 is problematic in processing the samples of many patients because it has throughput of about 126 μl/min per channel. In order to solve this problem, the parallel MOFF channels 200 are connected in parallel as in FIG. 9 so that several MOFF channels are integrated into one chip and high capacity separation is possible. Here, the central passages of the parallel MOFF channels 200 can be connected to the one passage 240 and may be combined with the dielectrophoresis channel 120 of FIG. 1.

Figure 10:
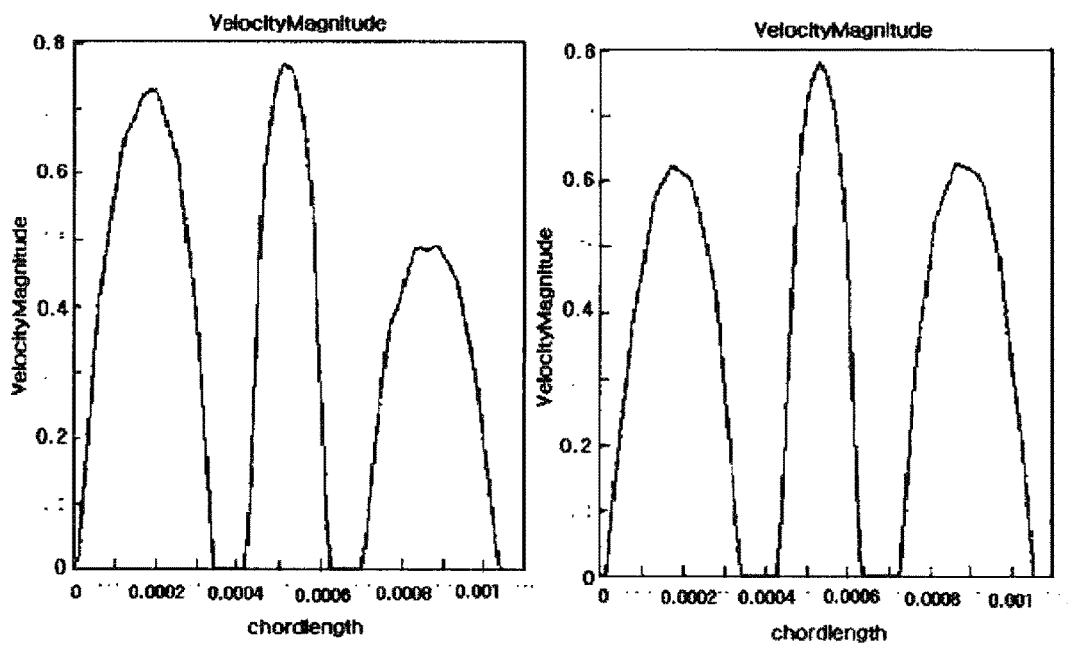
FIG. 10 is a graph showing of flow velocity of a fluid for illustrating the same flowing condition when the parallel MOFF channels in accordance with an embodiment of the present invention are used.

However, the parallel MOFF channels 200 must have a flow condition, such as four channels, for example, as in the case where the channels are driven independently. First, the design can be easily performed by symmetrically disposing connection channels branched from the inlet 210 of the channel to the four MOFF channels. In this case, the design of a drain unit through which samples are drained after the samples are branched into the MOFF channels becomes more complicated. Simulation results of FIG. 10 show that flow velocity (left graph) before fluid resistance of the connection channels 200 connected to the outlet 240 was controlled was asymmetrical in lower channels on the left and right, whereas flow velocity (right graph) after the fluid resistance was controlled was symmetrically stable on the left and right.

The following results, such as Table 2, were obtained as a result of attempts to separate CTCs of breast cancer and colorectal cancer, HT-29, or a cancer cell line, such as MCF-7, using the parallel MOFF channels 200. About 89.2% of white corpuscles (WBC) could be separated in the case of MCF-7 under a condition in which 90.8% of white corpuscles (WBC) could be removed, and cells of 80.7% could be separated in the case of HT-29. Since HT-29 and MCF-7 were very different in their sizes, separation efficiency of HT-29 was low, but optimal results were obtained by controlling the w value of FIG. 4 according to the type of cancer cells.

TABLE 2

|        | Outlet | Waste |
|--------|--------|-------|
| MCF-7  | 89.2%  | 10.8% |
| HT-29  | 80.7%  | 19.3% |
| WBC    | 9.2%   | 90.8% |

Figure 11:
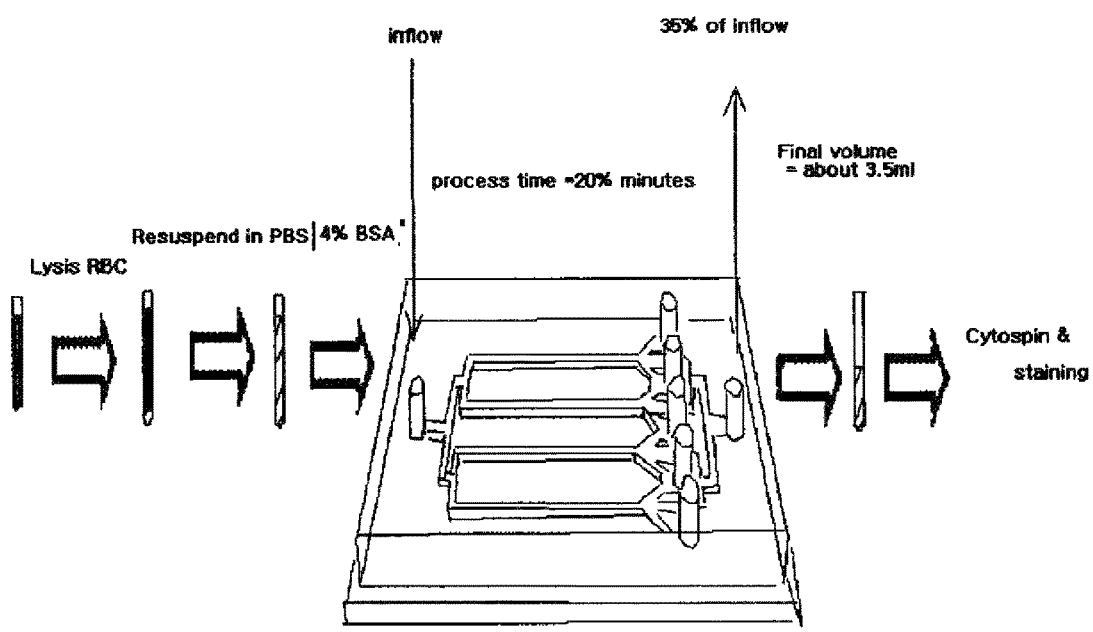
FIG. 11 is a diagram illustrating throughput when a red cell hemoclastic is used.

Furthermore, in order to improve throughput, the above-described fluid (blood) samples may be blood samples that have been pre-processed using red cell hemoclastic. The MOFF channel 110 has a limit that separation efficiency for cells having a specific concentration or higher is low. Accordingly, in order to separate blood, the blood needs to be diluted at a concentration of a specific level or lower. Here, dilution of about 100 times is required. In order to separate the diluted blood using the MOFF channel 110, a separation time of 52 hours or more is necessary, and it is also difficult to dilute the amount of finally separated samples, that is, 200 ml. Here, if most of red cells are removed using red cell hemoclastic, the separation time can be significantly reduced to 1.3 hour and can be applied to analysis in various ways using a Cytospin method having the final amount of final samples of 5 ml or less. Furthermore, if blood pre-processed using red cells hemoclastic as in FIG. 11 is separated using the parallel MOFF channels 200, the separation time is further reduced. For example, if four MOFF channels are connected in parallel and used, throughput can have 0.5 ml per minute, and thus CTCs can be separated from blood of a patient within about 20 minutes.

As a result of the separation of CTCs from the blood of a breast cancer patient through the blood processing process of FIG. 11, CTCs were actually successfully separated from the patient blood. Red cells (RBC) were primarily removed from blood 5~7.5 ml of the patient using hemoclastic, the blood from which red cells (RBC) were removed was injected into the inlet 210 of the parallel MOFF channels 200 at flow velocity of about 600 μl/min, and at the same time, the blood was discharged at a specific ratio (e.g., 35~40% of the inlet flow velocity) by controlling the flow velocity of the outlet 240. After the blood was separated, finally gathered samples of 3.5 ml were fixed to slide glass using Cytospin and dyed with DAPI, EpCAM, and CD45, and CTCs were checked. The results of the check show that the nuclei of cells were dyed in blue by means of DAPI, CTCs (right cells in the drawing) were dyed into epithelial cell in green by means of EpCAM, and white corpuscles (WBC) (left and central cells in the drawing) were dyed in red by means of CD45.

As described above, although the present invention has been described in connection with the limited embodiments and drawings, the present invention is not limited to the embodiments, and those skilled in the art to which the present invention pertains may modify and change the present invention in various ways from such a description. Accordingly, the scope of the present invention should not be limited to the aforementioned embodiments, but should be defined by the claims and equivalent thereof.

INDUSTRIAL APPLICABILITY

In accordance with the high-efficiency cell separation apparatus and method according to the present invention, cancer cells, that is, target cells, such as Circulating Tumor Cells (CTCs) (e.g., CTCs of breast cancer and colorectal cancer, HT-29, or a cancer cell line, such as MCF-7) within blood, can be more efficiently separated from fluid samples, such as blood.

The invention claimed is:

1. A particle separation apparatus comprising:
    a Multi-Orifice Flow Fractionation (MOFF) channel including a multi-orifice segment through which a fluid sample passes and discharging primarily separated materials from which target particles within the fluid sample have been separated through a central passage; and
    a dielectrophoresis channel including electrode pairs to which AC power is applied, forming an electric field in a flow channel connected to the central passage of the MOFF channel, and separating again the target particles from the primarily separated materials, which are discharged from the central passage of the MOFF channel, using dielectrophoresis, wherein the electrode pairs include one or more first electrode pairs and one or more second electrode pairs,
    wherein the dielectrophoresis channel comprises:
        a focusing unit equipped with the one or more first electrode pairs and configured to have target particles of the fluid sample, which are separated from the MOFF channel, concentrated at a center of the flow channel; and
        a second separation unit equipped with the one or more second electrode pairs and configured to have the target particles separate by the electric field, wherein the second separation unit is downstream of the focusing unit,
    wherein the one or more first and second electrode pairs are V-shaped with the point of the V of the one or more first electrode pairs pointing upstream on the dielectrophoresis channel and the point of the V of the one or more second electrode pairs pointing downstream on the dielectrophoresis channel, and the one or more first electrode pairs are symmetrical about a crosswise axis with the one or more second electrode pairs.

2. The particle separation apparatus of claim 1, wherein the MOFF channel comprises:
    an inlet having the fluid sample inputted thereto;
    a filter removing alien substances from the fluid sample inputted through the inlet; and
    a first separation unit discharging a fluid sample, including a plurality of the target particles, to the central passage after the fluid sample passing through the filter passes through the multi-orifice segment, and discharging a fluid sample, including a plurality of particles other than the target particles, to the passages on both sides thereof.

3. The particle separation apparatus of claim 1, wherein a diameter of an exit of the central passage has a greater diameter than a diameter of an entrance of the central passage.

4. The particle separation apparatus of claim 1 or 2, wherein the AC power is selectively applied in a range of a frequency 100~900 kHz within a range of 10~100 volts.

5. The particle separation apparatus of claim 4, wherein the target particle is a cell.

6. The particle separation apparatus of claim 5, wherein the cell is a Circulating Tumor Cell (CTC).

7. The particle separation apparatus of claim 6, wherein the CTC is a CTC of breast cancer or colorectal cancer, FIT-29, or a cancer cell line of MCF-7.

8. The particle separation apparatus of claim 1 or 2, wherein the target particles comprise any one of red cells, emulsion red cells, multiple osteomyelitis and multiple myeloma.

9. The particle separation apparatus of claim 1 or 2, wherein:
   the target particles are stem cells, and
   the particle separation apparatus separates stem cells from a fluid in which stem cells and normal cells are mixed.

10. The particle separation apparatus of claim 1 or 2, wherein:
   the target particles are bacteria, and
   the particle separation apparatus separates bacteria from a fluid in which dust and bacteria are mixed.

\* \* \* \* \*